US00PP37245P2

(12) United States Plant Patent
Ammerlaan

(10) Patent No.: US PP37,245 P2
(45) Date of Patent: Feb. 3, 2026

(54) ***ALOE* PLANT NAMED 'OVROCKS14'**

(50) Latin Name: *Aloe aristata*
Varietal Denomination: OVROCKS14

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 18/831,546

(22) Filed: Apr. 11, 2025

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Shubo Zhou
*Assistant Examiner* — Zachariah Allan Kay
(74) *Attorney, Agent, or Firm* — Samuel R. McCoy, Jr.

(57) ABSTRACT

A new and distinct *Aloe aristata* cultivar named 'OVROCKS14' which is characterized by compact erect foliage arranged in a basal rosette that relaxes as the plant matures, foliage that is a gradient of yellow-green, green, to greyed green which is densely covered with large greyed-green protuberances and prominent spines along the margins, mucronate laminar tips that develop from white to greyed-orange with maturation, and the stability of these characteristics from generation to generation.

4 Drawing Sheets

Latin name of the genus and species: The Latin name of the genus and species of the novel variety disclosed herein is *Aloe aristata.*

Variety denomination: The inventive variety of *Aloe* disclosed herein has been given the variety denomination 'OVROCKS14'.

BACKGROUND OF THE INVENTION

Parentage: 'OVROCKS14' is a seedling selection resulting from the controlled pollination of the seed parent, *Aloe aristata* '28' (not patented), and *Aloe aristata* '35' (not patented), the pollen parent. In 2015, the inventor initiated the crossing at a commercial greenhouse in Bleiswijk, the Netherlands. Both parents were developed by the inventor and never released to the public. The resulting seedlings were grown to maturity to evaluate for desirable characteristics. In 2017, one of the plants was observed to exhibit compact foliage that becomes outreaching as the plant matures, white mucronate laminar tips which mature into a greyed-orange color and prominent greyed-green protuberances relative to the parents and other progeny. The plant was isolated for further evaluation in order to confirm the distinctness and stability of the characteristics first observed. Upon confirmation of distinctness and stability, 'OVROCKS16' was selected for commercialization in 2017.

Asexual Reproduction: Asexual reproduction of the new cultivar 'OVROCKS14', by way of rooting leaf cuttings, was first initiated in the summer of 2017 at the inventor's commercial greenhouse in Bleiswijk, the Netherlands. The claimed plant has since been asexually propagated by way of meristematic tissue culture propagation. Through eight subsequent generations, the unique features of this cultivar have proven to be stable and true to type.

SUMMARY OF THE INVENTION

The cultivar 'OVROCKS14' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVROCKS14'. These characteristics in combination distinguish 'OVROCKS14' as a new and distinct *Aloe aristata* cultivar:

1. 'OVROCKS14' exhibits compact erect foliage arranged in a basal rosette that relaxes as the plant matures; and
2. 'OVROCKS14' exhibits foliage colored in a gradient of yellow-green, green to greyed-green, which is densely covered with large, prominent protuberances on both the adaxial and abaxial surfaces, and large prominent spines along the margins; and
3. 'OVROCKS14' exhibits white mucronate laminar tips which change in coloration to greyed-orange as the plant matures.

BOTANICAL DESCRIPTION OF THE PLANT

Figure 1:
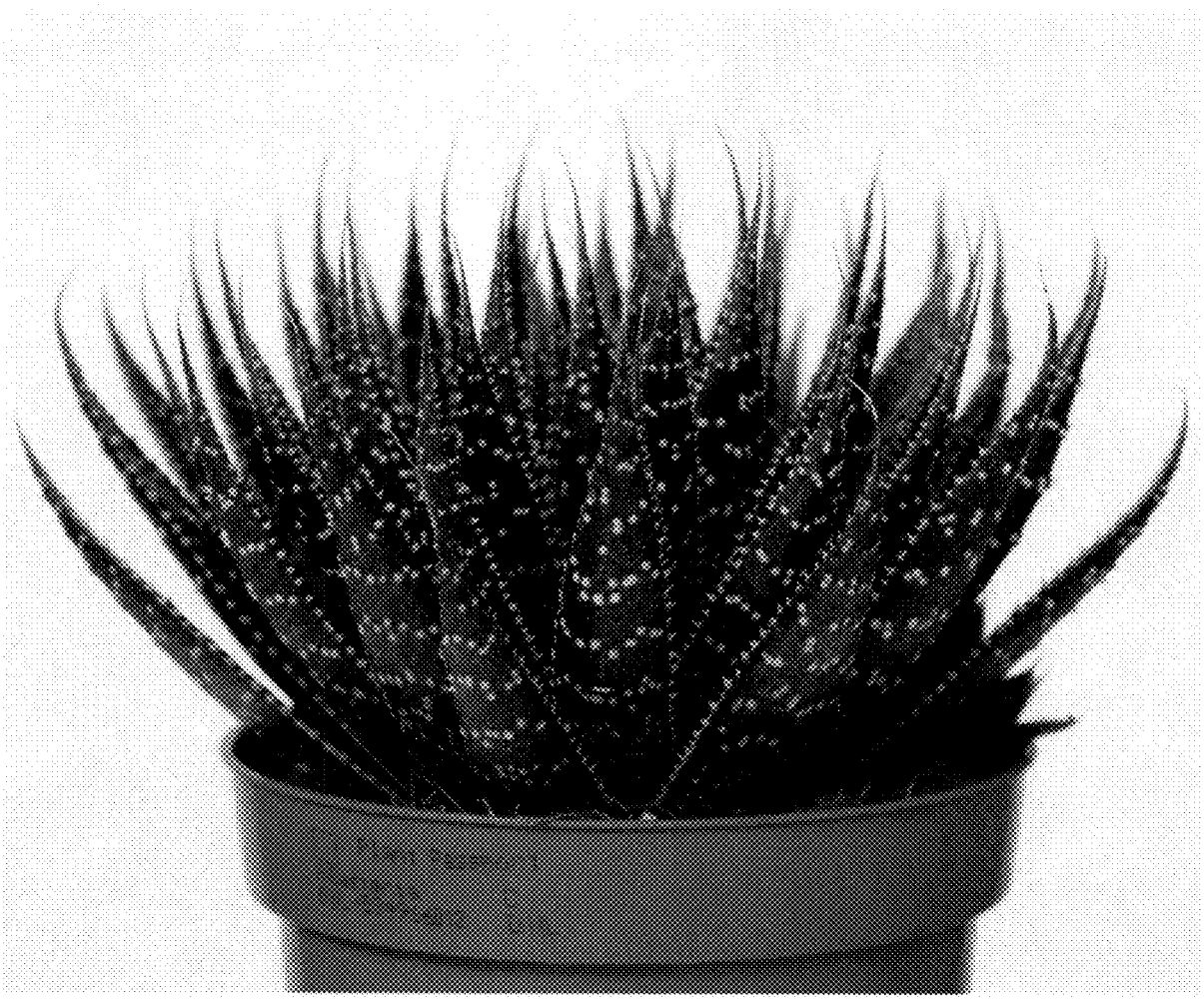
FIG. 1 illustrates, as nearly true as it is reasonably possible to make the same in color photographs of this type, an exemplary plant of 'OVROCKS14' grown in a commercial greenhouse in Heerhugowaard, the Netherlands. This plant is approximately 36 months old, shown planted in a 12 cm container.
Figure 2:
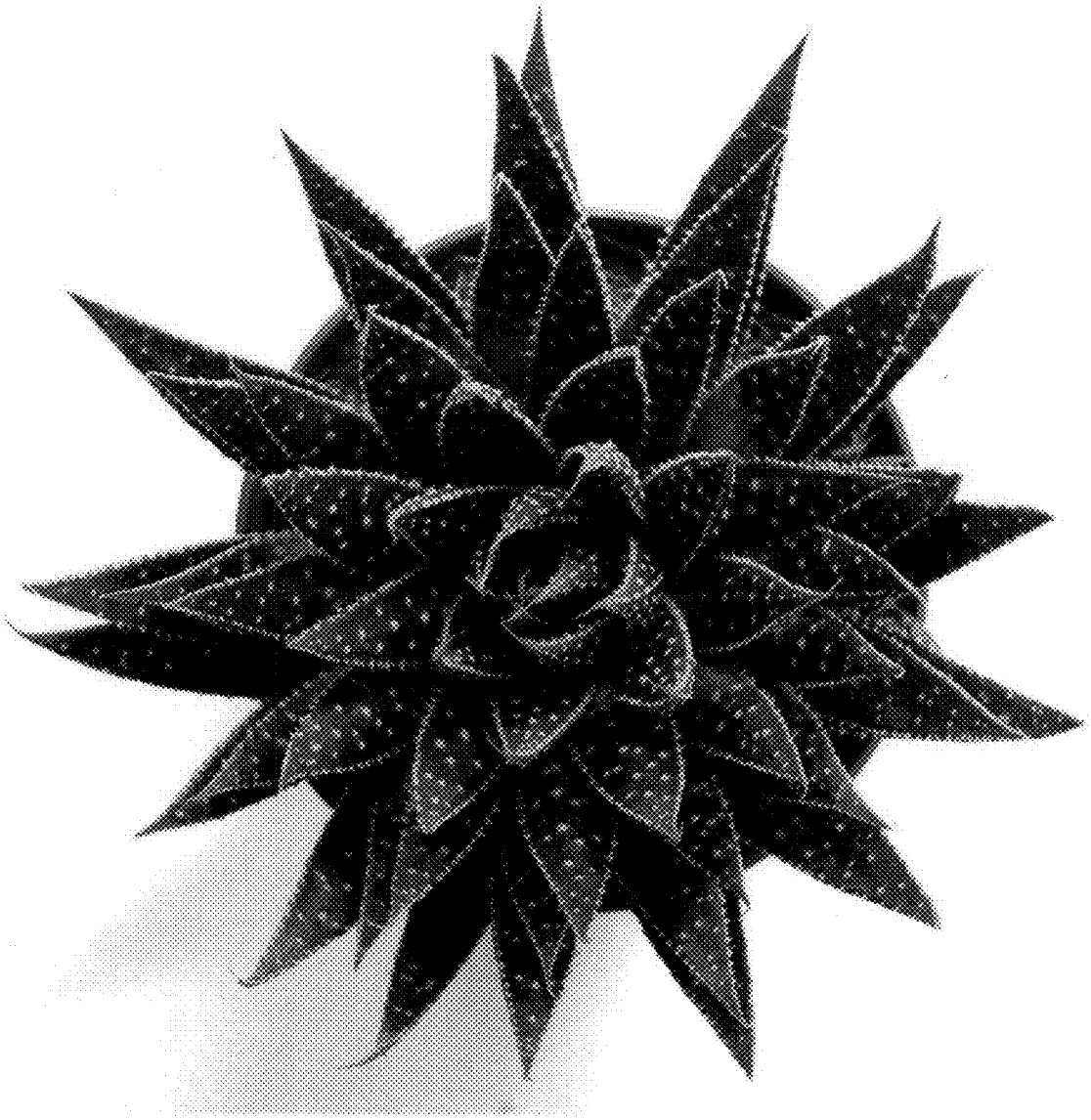
FIG. 2 illustrates, as nearly true as it is reasonably possible to make the same in color photographs of this type, the typical foliage arrangement of 'OVROCKS14'.
Figure 3:
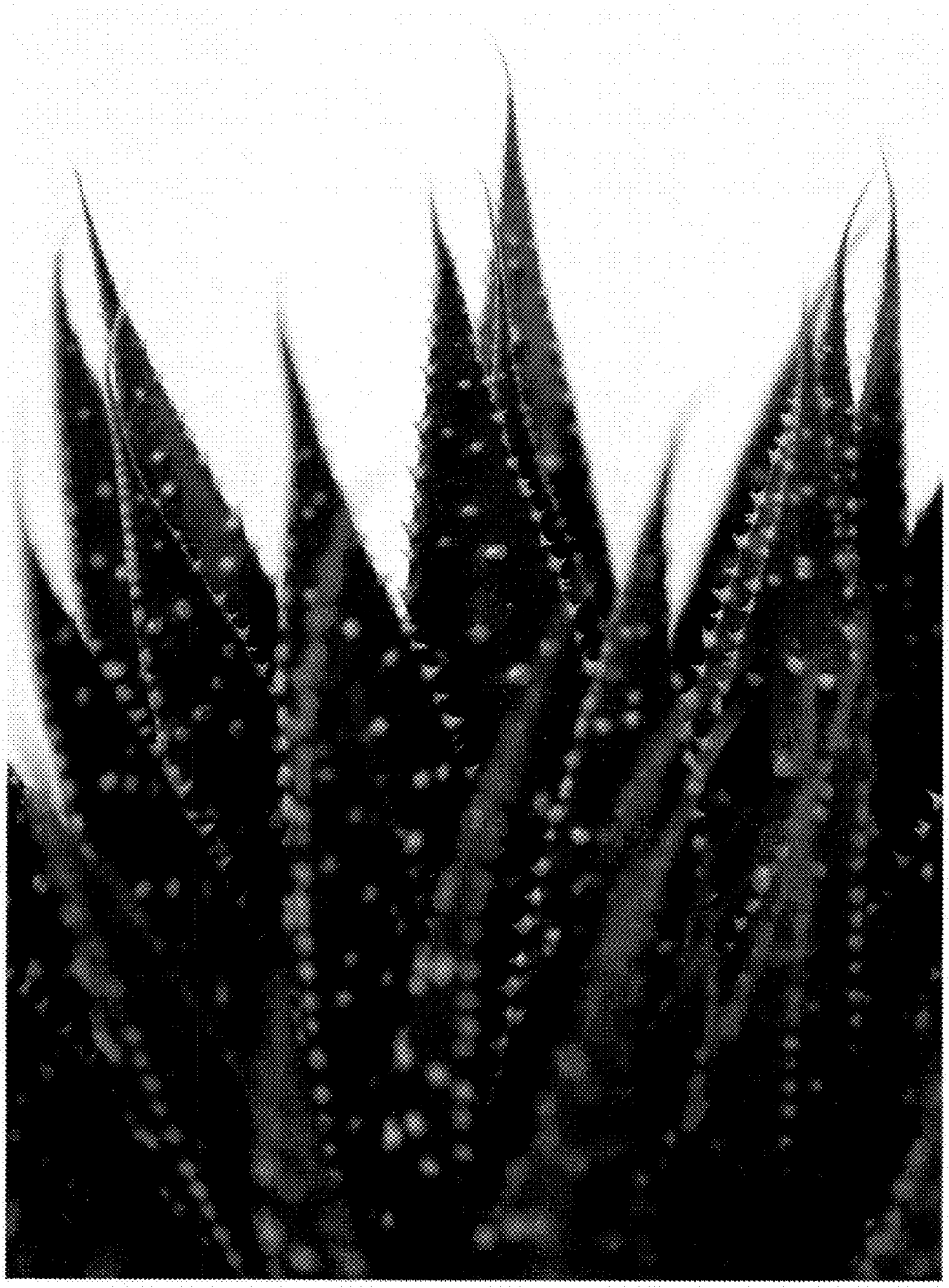
FIG. 3 illustrates, as nearly true as it is reasonably possible to make the same in color photographs of this type, the adaxial surface of the mature foliage 'OVROCKS14'.
Figure 4:
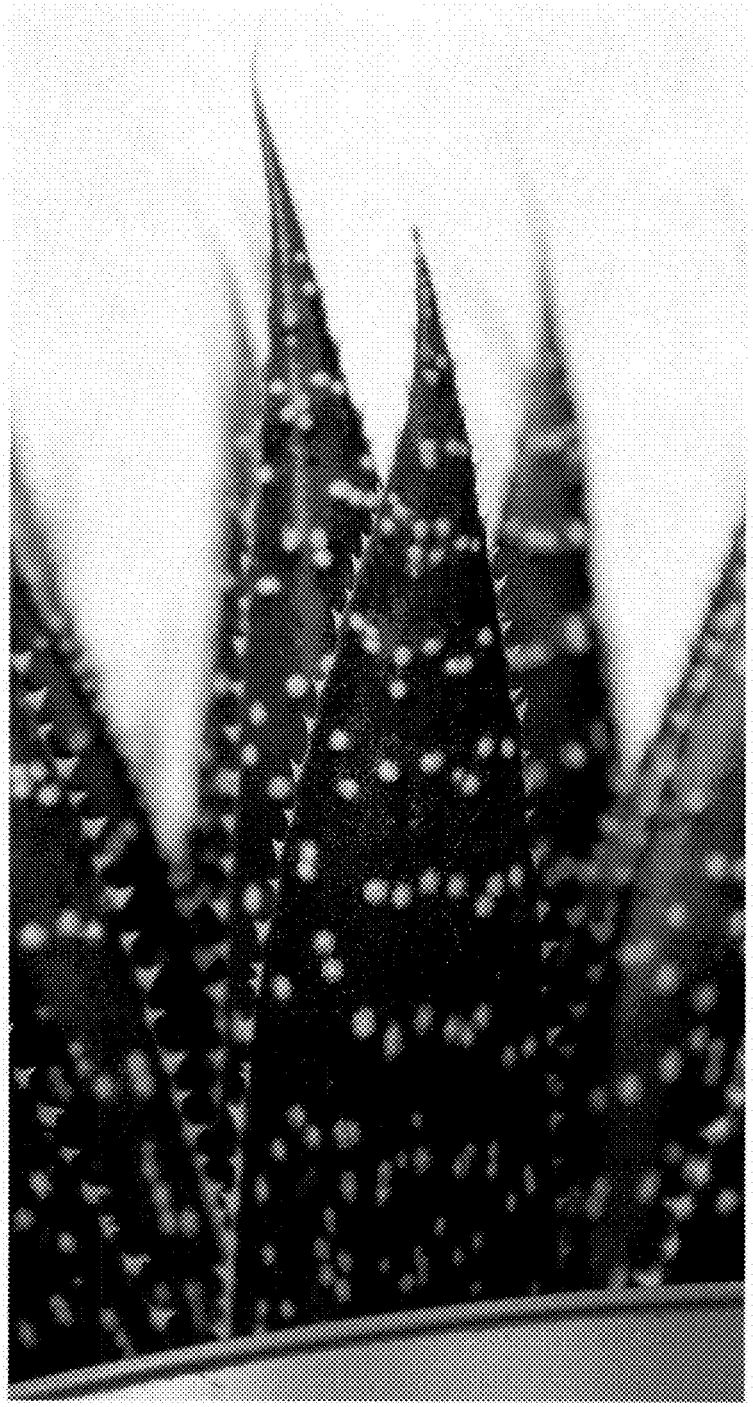
FIG. 4 illustrates, as nearly true as it is reasonably possible to make the same in color photographs of this type, the abaxial surface of the mature foliage 'OVROCKS14'.

The following observations and measurements made in October of 2016 describe averages from a sample set of six specimens of 36-month-old 'OVROCKS14' plants grown in 12 cm nursery containers at commercial greenhouse in Heerhugowaard, the Netherlands. Plants were produced using conventional greenhouse production protocols for *Aloe* which consisted of minimal irrigation and fertilizer applications, and chemical pest and disease control measures against mealy bug and *Botrytis* as required. Plants were grown under approximately 50 percent shade and no photoperiodic treatments or artificial light was given to the plants.

Those skilled in the art will appreciate that certain characteristics will vary with older or, conversely, with younger plants. 'OVROCKS14' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, Sixth Edition.

A botanical description of 'OVROCKS14' and a comparison with the parents and closest known comparator is provided below.

Plant description:

*Growth habit*.—Succulent perennial with foliage growing in a non-branched basal rosette.

*Plant shape*.—Globular to flattened globular.

*Height from soil level to top of foliar plane*.—11.6 cm.

*Plant spread*.—Average of 16.9 cm.

*Propagation*.—Type — Leaf cuttings and meristematic tissue culture. Time to initiate rooting — Approximately 28 to 35 days at 18 degrees Celsius. Time to produce a rooted mature plant — Approximately 18 to 22 weeks grown in a 14 cm container.

*Disease and pest resistance or susceptibility*.—Neither resistance nor susceptibility to typical *Aloe aristata* pests and diseases has been observed.

*Environmental tolerances*.—Adapt to, at least, USDA Zones 10 to 12 and temperatures as high as 40 degrees Celsius.

Root system:

*General*.—Fine fibrous roots.

Stems:

*Branching habit*.—Leaves in a non-branching basal rosettes; no main branches or lateral branches present.

Foliage:

*Arrangement*.—Rosette.

*Division*.—Simple.

*Attachment*.—Sessile.

*Quantity*.—Approximately 64 leaves per rosette.

*Shape*.—Lanceolate.

*Dimensions*.—8.9 cm long, 2.2 cm wide, and 0.8 cm thick, on average.

*Aspect*.—Flat to very slightly concaved with leaf tips curled upwards at an approximate angle of 20 degrees to the lamina.

*Attitude*.—Erect younger foliage in the inner whorls of the rosette, foliage becomes progressively more relaxed towards the outer whorls of the rosette. The average angle mature foliage is held at is approximately 65 degrees from horizontal.

*Apex*.—Narrow acute with a soft mucronate tip.

*Base*.—Broad cuneate.

*Margin*.—Finely serrate-dentate; marginal spines are 1.2 mm long on average; not undulated.

*Texture, adaxial surface*.—Glabrous, non-rugose, and moderately covered with large orbicular protuberances, each approximately 0.2 mm high at the base gradually becoming taller distally, average height is 0.75 mm at the tip of the lamina; 1.25 mm in diameter; protuberances occasionally bearing spines.

*Texture, abaxial surface*.—Glabrous, non-rugose, and covered with large oblong protuberances, more or less arranged in transverse rows; each protuberance is approximately 0.1 mm high and 1.8 mm in diameter; protuberances occasionally bearing spines which are approximately 0.5 mm high.

*Color*.—Juvenile foliage, adaxial surface — Yellow-green, nearest to RHS 147A, and fading to greyed-green towards the base, nearest to a blend of RHS 197A and 197B, transmuting to green, nearest to RHS NN137B, distally, mucronate tip is white, nearest to RHS N155B; protuberances are colored greyed-green, RHS 196C and 196D. Juvenile foliage, abaxial surface — Yellow-green, nearest to RHS 147A, and fading to grey-brown towards the base, nearest to a blend of RHS 199B and 199C, transmuting to green, nearest to RHS NN137B, distally, mucronate tip is white, nearest to RHS N155B; protuberances are colored greyed-green, RHS 196C and 196D. Mature foliage, adaxial surface — Green to yellow-green, nearest to a blend of RHS NN137A and 147A, and fading to greyed-green towards the base, nearest to RHS 198A, mucronate tip is greyed-orange, nearest to a blend of RHS 165C and 165D; protuberances are colored greyed-green, nearest to RHS 190B and 190D. Mature foliage, abaxial surface — Green to yellow-green, nearest to a blend of RHS NN137A and 147A, fading to greyed-green towards the base, nearest to RHS 197B; mucronate tip is greyed-orange, nearest to a blend of RHS 165C and 165D; protuberances are colored greyed-green, nearest to RHS 190D. Venation — No venation is visible.

*Petiole*.—No petiole; leaves are sessile.

Inflorescence: No flowering has been observed to date.

COMPARISONS WITH THE PARENT PLANTS

Plants of the new cultivar 'OVROCKS14' differ from the seed parent, *Aloe aristata* '28' (not patented), in the following characteristics described in Table 1 below.

TABLE 1

Comparison Between 'OVROCKS14' and The Seed Parent

| Characteristic | 'OVROCKS14' | '28' |
|---|---|---|
| General coloration of mature foliage. | A gradient of yellow-green, green to greyed-green, darker than '28'. | Lighter green than 'OVROCKS14'. |
| Leaf shape. | Shorter, more lanceolate than '28'. | Taller, broader linear than 'OVROCKS14'. |
| Leaf attitude | Foliage is relaxed and spreading as the plant matures, grows in a | Foliage is more relaxed than 'OVROCKS14'. |

TABLE 1-continued

| Comparison Between 'OVROCKS14' and The Seed Parent | | |
|---|---|---|
| Characteristic | 'OVROCKS14' | '28' |
| | compact whorl from the center of the basal rosette. | |

Plants of the new cultivar 'OVROCKS14' differ from the pollen parent, *Aloe aristata* '35' (not patented), in the following characteristics described in Table 2 below.

TABLE 2

| Comparison Between 'OVROCKS14' and The Pollen Parent | | |
|---|---|---|
| Characteristic | 'OVROCKS14' | '35' |
| General coloration of mature foliage. | A gradient of yellow-green, green to greyed-green. | Darker green than 'OVROCKS14'. |
| Leaf shape. | Taller, more lanceolate than '35'. | Shorter, more ovate than 'OVROCKS14'. |
| Leaf attitude | Foliage is relaxed and spreading as the plant matures, less erect than '35'. | Foliage is compact, grows more erect from the center of the basal rosette than 'OVROCKS14'. |

COMPARISONS WITH THE CLOSEST KNOWN COMPARATOR

Plants of the new cultivar 'OVROCKS14' differ from the commercial variety, *Aloe* 'AMIAL 1619' (U.S. Plant Pat. No. 28,947) in the following characteristics described in Table 3 below.

TABLE 3

| Comparison Between 'OVROCKS14' and 'AMIAL1619' | | |
|---|---|---|
| Characteristic | 'OVROCKS14' | 'AMIAL 1619' |
| Leaf thickness. | Thinner and less robust than 'AMIAL 1619'. | Broader and thicker than 'OVROCKS14'. |
| General coloration of mature foliage. | Green to yellow green and suffused with greyed-green. | Lighter green than 'OVROCKS14'. |
| Leaf protuberances. | Large, prominent protuberances that are greyed-green in color and occasionally bearing small spines on the abaxial leaf surface. | Protuberances appear more prominent as more protuberances bear taller spines than 'OVROCKS14' on the abaxial leaf surface. |

That which is claimed is:

1. A new and distinct variety of *Aloe aristata* plant named 'OVROCKS14', substantially as described and illustrated herein.

* * * * *